(12) United States Patent
Lei

(10) Patent No.: US 11,903,853 B2
(45) Date of Patent: Feb. 20, 2024

(54) GUIDEWIRE ADJUSTER AND DELIVERY-SYSTEM CONTROL HANDLE

(71) Applicant: VENUS MEDTECH (HANGZHOU), INC., Zhejiang (CN)

(72) Inventor: Rongjun Lei, Hangzhou (CN)

(73) Assignee: VENUS MEDTECH (HANGZHOU) INC., Hangzhou (CN)

( * ) Notice: Subject to any disclaimer, the term of this patent is extended or adjusted under 35 U.S.C. 154(b) by 196 days.

(21) Appl. No.: 17/542,267

(22) Filed: Dec. 3, 2021

(65) Prior Publication Data

US 2022/0096256 A1 Mar. 31, 2022

Related U.S. Application Data

(63) Continuation of application No. 16/442,032, filed on Jun. 14, 2019, now Pat. No. 11,197,772, which is a continuation of application No. PCT/CN2017/111049, filed on Nov. 15, 2017.

(51) Int. Cl.
| | |
|---|---|
| *A61F 2/95* | (2013.01) |
| *A61B 17/00* | (2006.01) |
| *A61F 2/24* | (2006.01) |
| *A61M 25/09* | (2006.01) |

(52) U.S. Cl.
CPC .......... *A61F 2/95* (2013.01); *A61B 17/00234* (2013.01); *A61F 2/2439* (2013.01); *A61M 25/09* (2013.01); *A61B 2017/00243* (2013.01); *A61F 2/2436* (2013.01)

(58) Field of Classification Search
CPC ........ A61F 2/95; A61F 2/2439; A61F 2/2436; A61F 2/9517; A61B 17/00234; A61B 2017/00243; A61B 2017/1209; A61B 2017/12095; A61B 2017/12068; A61M 25/09; A61M 25/09041; A61M 25/0905; A61M 2025/09125
See application file for complete search history.

(56) References Cited

U.S. PATENT DOCUMENTS

| | | | | |
|---|---|---|---|---|
| 4,858,810 A | * | 8/1989 | Intlekofer | A61B 17/3403 24/115 M |
| 5,325,868 A | * | 7/1994 | Kimmelstiel | A61B 17/22 600/585 |
| 2014/0249540 A1 | * | 9/2014 | Nieman | A61B 17/221 606/113 |

* cited by examiner

*Primary Examiner* — Erich G Herbermann

(57) ABSTRACT

The present invention provides a guidewire adjuster and a delivery-system control handle provided with the guidewire adjuster. The guidewire adjuster includes a support mechanism which has a lumen for a guidewire to extend therethrough; and a driving mechanism for driving the guidewire to move back and forth in the lumen. The guidewire adjuster is able to drive the guidewire to move with respect to a sheath of the delivery system. The support mechanism is connected to the control handle of the delivery system and forms a lumen for accommodating the guidewire. A proximal end of the sheath together with the stent can be driven to move upwardly, due to the relative movement between the guidewire and the sheath of the delivery system. Therefore, the position of the stent can be adjusted by advancing the guidewire forward when the stent has been deployed at a lower position than expected.

16 Claims, 5 Drawing Sheets

GUIDEWIRE ADJUSTER AND DELIVERY-SYSTEM CONTROL HANDLE

TECHNICAL FIELD

The present invention relates to the technical field of medical apparatus and instruments, and in particular to a delivery-system control handle and a guidewire adjuster that can be operated with the control handle.

BACKGROUND

Interventional clinical procedures have developed rapidly and widely in recent years as they involve less trauma and are less invasive to the human body, in which, a dedicated delivery system is usually required to deliver a medical device, and an implant device or the like to a lesion site.

A typical delivery system generally includes a sheath, a core shaft located in the sheath, and an operation handle. The core shaft usually includes a core tube, a stent fixing head, a mounting section, and a guide head connected in sequence along a direction away from the operator. In the process of implanting the implant device, a stent carrying a prosthesis valve is first secured to the stent fixing head through latching members at its end, and then the sheath is arranged surrounding the core shaft and forces the stent to a compressed configuration.

Referring to FIG. 1, taking an interventional aortic valve replacement procedure for example, a thin guidewire 1 is inserted into the body of a patient through the femoral artery or femoral vein. The leading end of the guidewire 1 enters the left ventricle 2 through the aortic valve, and is partially coiled and rested at the bottom of the left ventricle. The sheath loaded with a valve is then delivered to the aortic valve 3 along the guidewire 1, and the sheath is withdrawn to release the stent 4, which expands at body temperature.

As the expanded stent 4 assumes a tapered expansion configuration, the tapered outer wall would slide down under the pressing of the aortic valve 3, which would cause the valve on the stent 4 being positioned lower than expected, resulting in unsatisfactory clinical results. A known solution is to adjust the position of the stent by driving the sheath 5. However, such adjustment has an unsatisfactory performance due to the special configuration of the aortic arch.

Referring to FIG. 2 and FIG. 3, if the sheath 5 is withdrawn, the sheath 5 could be locked at the inner side of the bending portion of the aortic arch as indicated by the dotted line in FIG. 2, such that it is impossible to transmit the movement of the sheath to the stent.

However, if the sheath 5 is advanced forward, the sheath 5 could abut the outer side of the bending portion of the aortic arch as indicated by the dotted line in FIG. 3, and as a result, it is also impossible to transmit the movement to the stent.

In summary, it is difficult to adjust the position of the stent by operating the sheath. As a result, it is difficult to adjust the position of the stent with a conventional delivery system once the stent has been deployed in a lower position, which increases the risks of the clinical procedure.

SUMMARY

The present invention provides a guidewire adjuster which drives a shealth to move a stent by adjusting an axial position of the guidewire relative to the sheath during an interventional procedure, and the sheath together with the stent can be driven to move upwardly to position the stent and the valve at a predetermined position, especially when the position of the stent is lower than expected.

A guidewire adjuster comprises:

a support mechanism having a lumen for a guidewire to extend therethrough; and a driving mechanism for driving the guidewire to move back and forth in the lumen.

The guidewire adjuster according to the invention is able to drive the guidewire to move with respect to the sheath of the delivery system, wherein the support mechanism is connected with a control handle of the delivery system, and forms a lumen for receiving the guidewire. The shape and the structure of the guidewire adjuster are not limited, as long as it achieves the above indicated functions.

Optionally, the support mechanism includes a housing through which the lumen extends along a straight path or a curved path.

The guidewire preferably follows a linear motion within the support mechanism, however, a curved path, for example, an arced path partially or entirely along the support mechanism, may be possible under the allowance of the elasticity of the guidewire.

Optionally, the housing is provided with a fitting structure fixedly connectable with an operation handle of a delivery system.

The fitting structure is a threaded structure, a plug-in structure or a snap-on structure.

To facilitate convenient operation and smooth driving of the guidewire, the support mechanism and the control handle of the delivery system are preferably fixedly connected in use.

Optionally, the driving mechanism is configured as a manual driving mechanism, an electric driving mechanism or a pneumatic driving mechanism.

Optionally, at least a portion of the driving mechanism is located inside a housing of the support mechanism, or at least a portion of the driving mechanism is located outside the housing of the support mechanism.

To obtain a guidewire adjuster with a simpler profile and less spatial interference, the driving mechanism may be entirely arranged inside the support mechanism, or a portion of an operating component is located outside the support mechanism and connected thereto by, for example, insertion or the like.

Optionally, the driving mechanism comprises a force applying member in direct contact with the guidewire, and the force applying member is movable along the lumen or rotatable about an axis.

The axis is perpendicular to or inclined with respect to a corresponding portion of the lumen.

The movement of the guidewire is directly driven by the force applying member, and the guidewire moves along its own axis. The movement of the force applying member may be varied and provided that it can be converted into the axial movement of the guidewire by appropriate approaches.

Preferably, the support mechanism is configured as an inner tube, the driving mechanism is configured as an outer sleeve slidably mounted around the inner tube; and wherein one of the inner tube and the outer sleeve is provided with a connecting member at one end thereof, and the other one of the inner tube and the outer sleeve is provided with a locking mechanism at an end opposite from the connecting member, and the connecting member comprises a fitting structure fixedly connectable with the operation handle of the delivery system.

The guidewire adjuster according to the present invention is connected to and fixed relative to the operation handle in the delivery system through the connecting member. In use, the relative movement between the guidewire and the sheath (or the stent) in the delivery system is achieved by sliding the outer sleeve relative to the inner tube. When the position of the stent is lower than expected, the guidewire is advanced forward (towards the lesion site), and thus the length of the guidewire entering in the blood vessel is increased, which causes the sheath to move outwardly at the bending portion at the aortic arch. Since a length of the sheath inside the blood vessel is maintained, and the distal end of the sheath (the end distant from the lesion site) is fixed to the operation handle, the proximal end of the sheath is forced to drive the stent to move upwardly (towards an outer side of the bending portion) to adjust the position of the stent.

A Luer taper may usually be provided at the distal end of the operation handle, and accordingly, the connecting member may have an internal thread structure fitting with the Luer taper.

In order to fix the connecting member to the operation handle, and to facilitate the convenience of operation, optionally, the connecting member has a plug connectable with the operation handle. Accordingly, one end of the operation handle has a fitting configuration such as a socket or a jack that fits with the plug.

The outer sleeve is partially mounted around and overlaps with the inner tube, preferably one end of the inner tube is provided with a connecting member, and one end of the outer sleeve opposite from the connecting member is provided with a locking mechanism.

Optionally, the locking mechanism comprises an axial bearing member detachably connected to the guidewire, and a driving member provided on the outer sleeve and connected to the axial bearing member.

The axial bearing member protrudes from the outer surface of the guidewire at least in the radial direction. The outer sleeve drives the axial bearing member to move through the driving member as it moves, and in turn drives the guidewire to move.

Preferably, the axial bearing member is locked to the guidewire by a screw or fixed to the guidewire by elastic clamping.

The driving member and the axial bearing member are axially positioned relative to each other, and the specific shapes of the driving member and the axial bearing member are not limited. For example, the driving member may be formed in one piece with the sleeve and the driving member may be connected to the axial bearing member by a connecting component, or a direct connection such as a plug-in connection or an interference fit, etc.

Optionally, the locking mechanism is configured as an abutment member inserted into a side wall of the outer sleeve, and one end of the abutment member extends into the lumen and abuts against the guidewire.

The abutment member may be a threaded pin or a resilient latch or the like, which locks the guidewire via a radial movement.

Preferably, the locking mechanism comprises at least two elastic hooks at the end of the outer sleeve for clamping the guidewire, and a pressing cap threadably engaged with the end of the outer sleeve to force the elastic hooks to converge towards each other. The elastic claw functions as a force applying member in direct contact with the guidewire.

As the pressing cap rotates, the elastic hooks are forced to converge towards each other and in turn lock the guidewire. The structure is convenient to operate and disassemble.

An inner wall of the pressing cap comprises a tapered surface for guiding the elastic hooks to converge towards each other, and the pressing cap is provided with a guidewire insertion hole at a central portion thereof.

In order to prevent the relative rotation of the inner tube and the outer sleeve, it is preferred that a circumferential limit mechanism is provided between the inner tube and the outer sleeve.

The circumferential limit mechanism comprises a guide groove extending axially in a side wall of one of the inner tube and the outer sleeve, and a limit pin provided on the other one of the inner tube and outer sleeve, and the limit pin is retained in the guide groove.

As an option, the circumferential limit mechanism comprises a guide groove extending axially and formed in the side wall of the inner tube, and a limit pin provided on the outer sleeve and extending into the guide groove.

The outer sleeve side wall is provided with a radial through hole, and the limit pin is fixedly engaged in the radial through hole.

In order to precisely adjust the axial position of the outer sleeve relative to the inner sleeve, it is preferred that the inner tube is threadably engaged with a driving sleeve which is rotatably connected to and axially positioned to the outer sleeve.

The threaded connection functions to adjust the axial position of the driving sleeve, and the precise control of the position of the guidewire can be achieved by moving the outer sleeve with the driving sleeve.

In order to achieve rotatable connection and axial positioning of the driving sleeve with respect to the outer sleeve, preferably, the inner wall of the driving sleeve is provided with an annular groove, and the outer wall of the outer sleeve is provided with a positioning member rotatably engaged in the annular groove.

When the driving sleeve rotates relative to the outer sleeve, the driving sleeve moves axially and drives the outer sleeve to move axially due to the engagement of the positioning member and the annular groove.

It is also possible to electrically drive the driving sleeve, and preferably, a driving motor is provided outside the inner tube, and the driving motor is connected to the driving sleeve in a way which more effectively transmits torque.

The driving sleeve can be driven by the driving motor to rotate clockwise or counterclockwise with a simple operation, by only requiring the control of a switch without manual rotation.

Optionally, the driving motor is connected to the driving sleeve with a gear transmission.

In order to facilitate manufacturing and installation, it is further preferable that the driving sleeve includes a threaded section connected to the inner sleeve, and an extension section mounted around the outer sleeve, wherein the threaded section and the extension section are fixed to each other by a plug-in connection.

The annular groove is located at a joint of the threaded section and the extension section.

As the inner tube and the outer sleeve move relative to each other, a portion of the outer sleeve may move away from the inner tube, which may result in shaking or bending. With an extension section mounted around the outer sleeve, the overall strength of the guidewire adjuster would be improved and thus bending or breaking of the inner tube or the outer sleeve may be avoided.

It is preferred that the outer wall of the driving sleeve has a textured surface to facilitate grip.

Preferably, the outer wall of the inner tube is provided with a scale for indicating an axial position of the driving sleeve.

The present invention further provides a delivery system comprising an operation handle forming a lumen therein for a guidewire to extend therethrough in an axial direction, and the guidewire adjuster according to the invention. The connecting member of the guidewire adjuster is fixedly connected to a distal end of the operation handle, and the lumen of the guidewire adjuster communicates with an inner lumen of the operation handle.

Preferably, the distal end of the operation handle is provided with a Luer taper, and the connecting member is configured as a nut secured to an end of the inner tube and engagable with the Luer taper.

Preferably, the distal end of the operation handle is provided with a socket, and the connecting member is a plug engagable with the socket.

Preferably, the support mechanism is a tubular housing, and the driving mechanism comprises:

a driving motor installed in the housing;

a slide block fixed to the guidewire; and a transmission mechanism connected between the driving motor and the slide block.

The driving motor located in the housing drives the slide block through the transmission mechanism, and thus drives the guidewire to move. The slide block may be connected to the guidewire by means of clamping, insertion with interference fit, or fastening members.

Optionally, the transmission mechanism is a screw-nut pair, with the screw connected to the output shaft of the driving motor, and the nut fixed to the slide block or integrally formed on the slide block as one piece.

Optionally, the transmission mechanism comprises a gear connected to the output shaft of the driving motor, and a rack fixed to the slide block or integrally formed on the slide block as one piece, wherein the gear and rack are engaged with each other.

The housing is provided with a guide groove for guiding the movement of the slide block.

The slide block follows linear movement in the case of a screw-nut pair or a gear and rack engagement. A guide groove may be provided to increase the stability of the movement of the slide block, alternatively, a guide rail or the like may be employed.

Optionally, the support mechanism is a tubular housing, and the driving mechanism comprises:

a driving motor installed in the housing;

two wheels rotatably mounted to the housing for cooperatively clamping the guidewire; and a driving mechanism connected between the driving motor and the two wheels.

The tubular housing is convenient to hold. For example, the housing may be cylindrical, and the outer wall thereof is provided with a textured surface or an uneven surface with protrusions and/or recesses to facilitate grip.

The transmission mechanism comprises two gears engaged with each other, and the two gears are respectively fixed to the two wheels, wherein one of the two gears is a driving gear which is directly or indirectly connected to the output shaft of the driving motor.

The outer peripheral surfaces of the two wheels are provided with teeth for engaging with the guidewire or one or more grooves for accommodating the guidewire.

In the case of electrical driving, a known control circuit can be provided for the motor. For example, a servo motor may be provided, and the back and forth movement of the guidewire is achieved by the motor rotating clockwise or counterclockwise.

The control circuit may be programmed to be controllable and, cooperating with an external sensor, controls the movement of the guidewire automatically in real time, so as to further increase the automation level.

For convenient operation, it is preferable to provide a control button for a driving motor on the housing.

Preferably, the housing is provided with a seal at a position through which the guidewire passes, to protect the components inside the support mechanism and avoid contamination.

The present invention further provides a delivery system control handle, which comprises a handle body provided with a lumen for a guidewire to extend therethrough, and the handle body is connected with a guidewire adjuster according to the invention. The handle body is connected to the support mechanism of the guidewire adjuster, and the lumen of the handle body and the lumen of the guidewire adjuster communicate with each other for the guidewire to extend therethrough.

According to the guidewire adjuster provided by the invention, if a stent has been deployed at a lower position than expected, the position of the stent can be adjusted by advancing the guidewire forward. Due to the relative movement between the guidewire and the sheath (or the stent) of the delivery system, a proximal end of the sheath as well as the stent can be moved upwardly.

DESCRIPTION OF THE EMBODIMENTS

Figure 1:
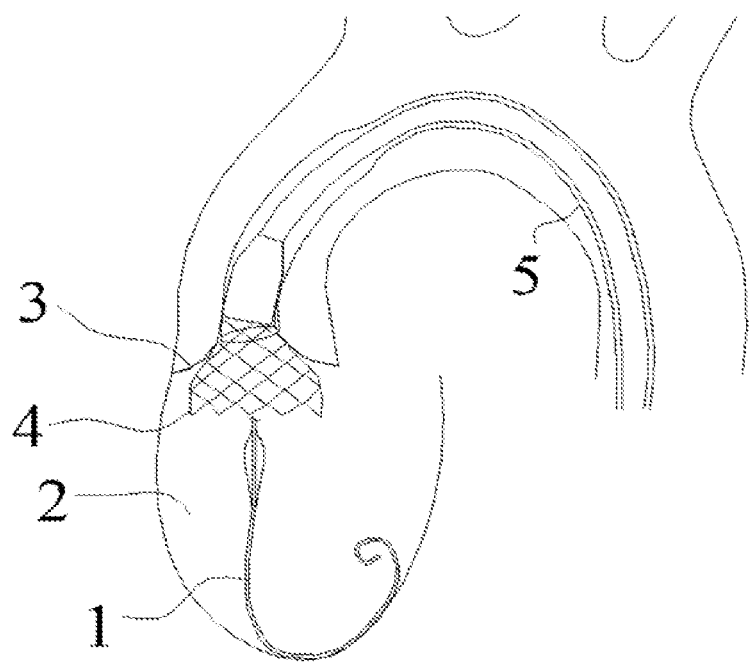
FIG. 1 is a schematic view showing a stent in the prior art deployed at a lower position at the aortic valve.
Figure 2:
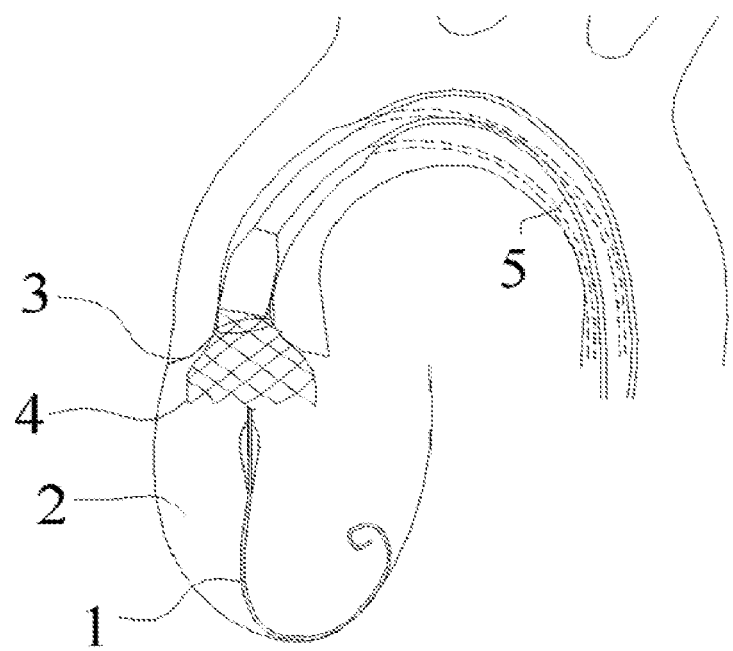
FIG. 2 is a schematic view showing the sheath of FIG. 1 having been withdrawn.
Figure 3:
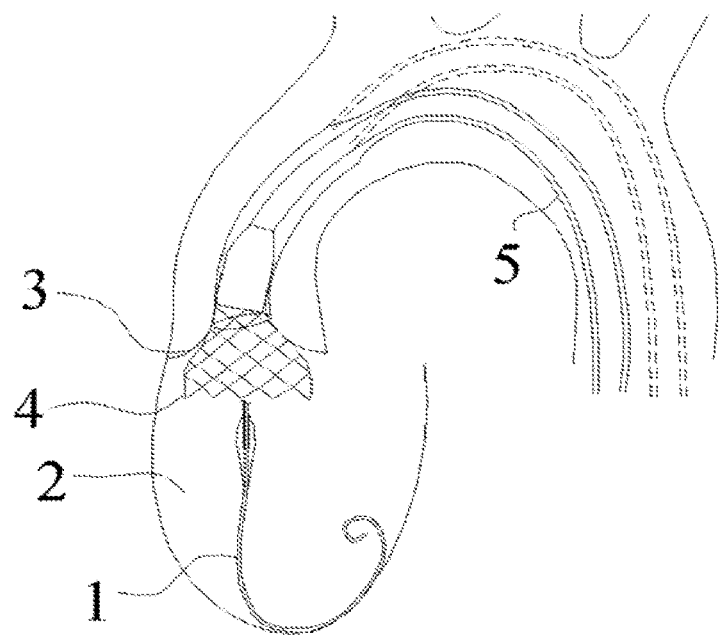
FIG. 3 is a schematic view showing the sheath of FIG. 1 having been advanced forward.
Figure 4:
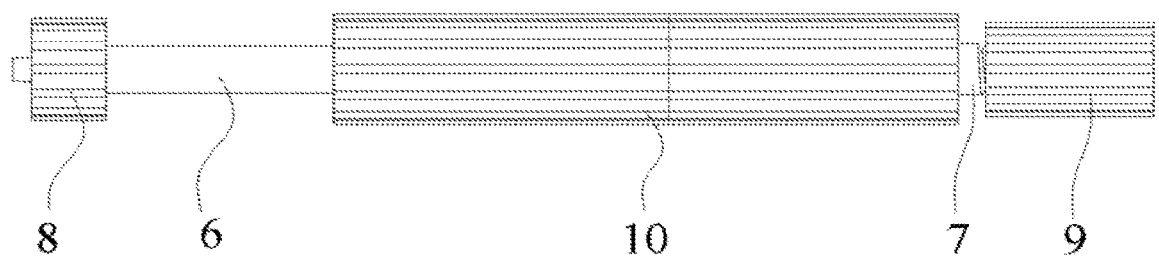
FIG. 4 is a schematic view of a guidewire adjuster according to an embodiment of the present invention, viewed from outside.

Referring to FIG. 4, a guidewire adjuster according to an embodiment of the present disclosure includes an inner tube 6 and an outer sleeve 7. The outer sleeve 7 is slidably mounted around the inner tube 6. Each of the inner tube 6 and the outer sleeve 7 is a hollow tubular structure, with an inner lumen for the guidewire to extend through.

The inner tube 6 and the outer sleeve 7 are partially overlapped with each other, and the outer sleeve 7 surrounds an outer periphery of the inner tube 6 at the overlapped portion.

An end of the inner tube 6 extends out of the outer sleeve 7, and is provided with a connecting member 8. An end of the outer sleeve 7 opposite from the connecting member 8 is provided with a locking mechanism 9. The inner tube 6 has an outer thread engagable with a driving sleeve 10, which is rotatably connected to the outer sleeve 7 and axially positioned thereto.

Figure 5:
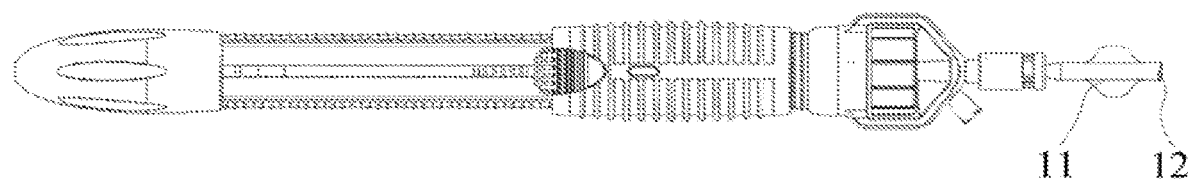
FIG. 5 is a structural schematic view of a delivery-system control handle adjuster according to an embodiment of the present invention, with the guidewire adjuster omitted.

Referring to FIG. 5, in this embodiment, a distal end of the delivery-system control handle is configured as a Luer taper 11 having an external thread 12 at its end.

Figure 6:
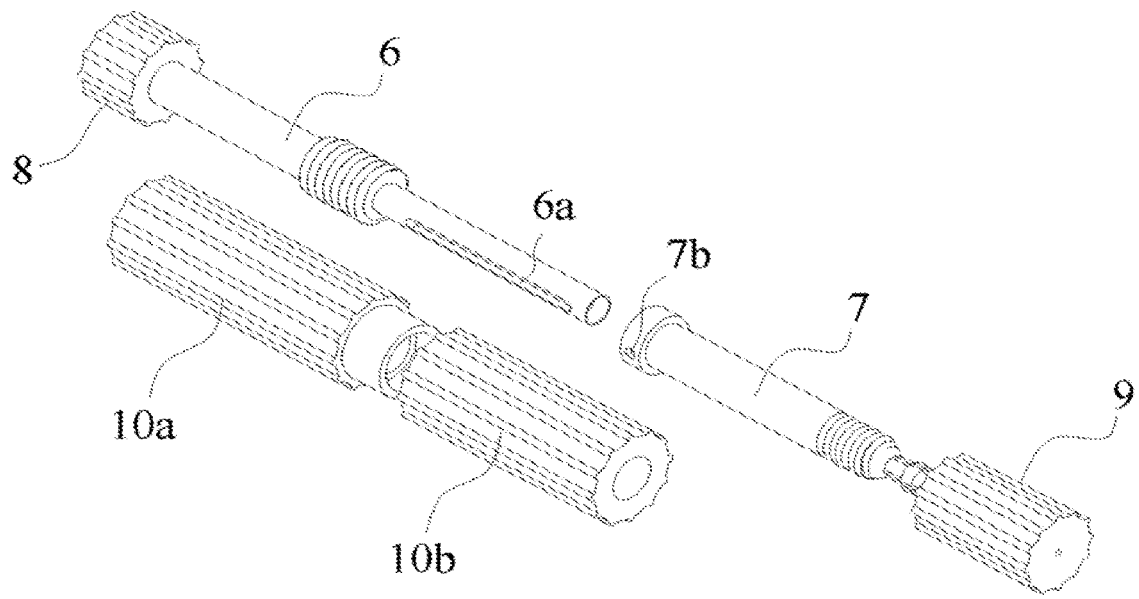
FIG. 6 is an exploded view of the guidewire adjuster according to the embodiment of the present invention.
Figure 7:
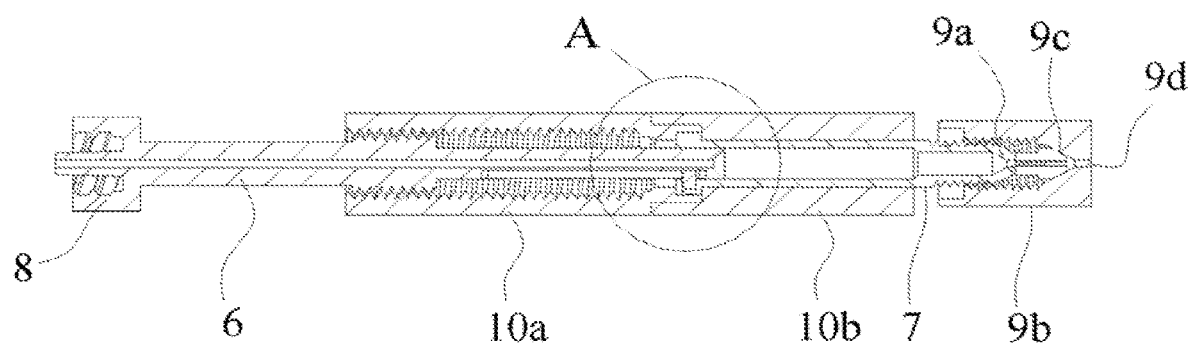
FIG. 7 is a cross-sectional view of the guidewire adjuster according to the embodiment of the present invention.
Figure 8:
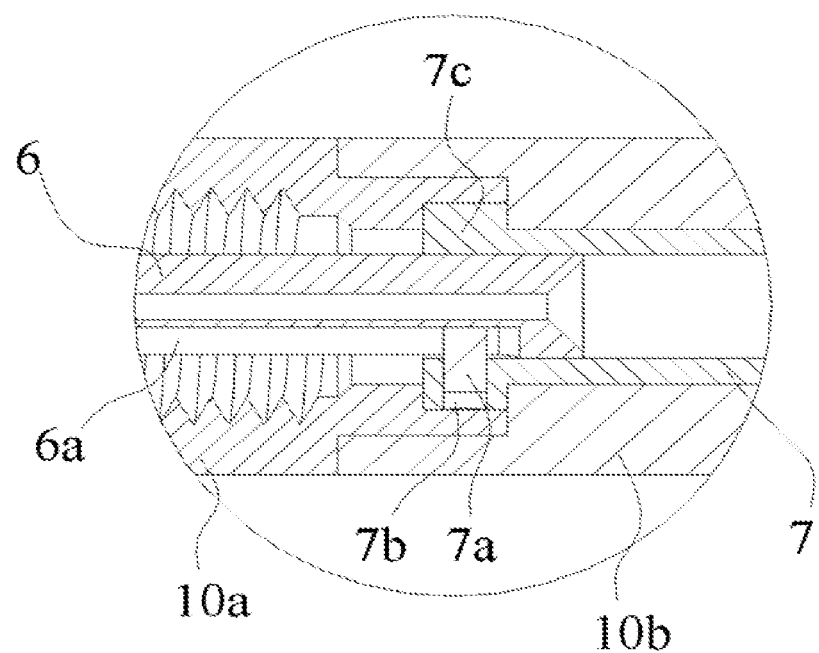
FIG. 8 is an enlarged view of portion A in FIG. 7.

Referring to FIGS. 6 to 8, the connecting member 8 is a nut fixed to the end of the inner tube and fitting with the Luer taper 11. The nut has an internal thread fitting with the external thread 12.

In use, the guidewire adjuster is connected to the Luer taper 11 via the connecting member 8. It should be understood that in other embodiments, the guidewire adjuster and the control handle may be fixed to each other by, for example, a plug-in connection. In that case, a socket may be provided in the control handle, and the connecting member may have a plug fitting with the socket.

The guidewire adjuster and the control handle may also be fixedly connected to each other by an additional connecting member, as long as they are connected in a detachable manner to facilitate the procedure.

The locking mechanism 9 functions to lock and position the guidewire with respect to the outer sleeve 7. The locking mechanism 9 includes four elastic hooks 9a at the end of the outer sleeve 7 for clamping the guidewire. It can be understood that the number of the elastic hooks may be less or more, for example three, to meet different requirements.

The end of the outer sleeve 7 is provided with an external thread, and the locking mechanism 9 further includes a pressing cap 9b which fits with the external thread of the outer sleeve to force the elastic hooks to converge towards each other. An inner wall of the pressing cap 9b includes a tapered surface 9c which guides the elastic hooks to converge towards each other. As the pressing cap 9b rotates, the elastic hooks converge towards each other under the pressing of the tapered surface, such that the elastic hooks cooperatively clamp and lock the guidewire. To allow the guidewire to extend through, the pressing cap 9b is provided with a through hole 9d at a central portion thereof.

Each elastic claw has a head which is provided with an inclined surface corresponding with the tapered surface 9c to facilitate automatically guiding of the elastic hooks and clamping and locking of the guidewire. The elastic hooks may be formed in one piece with the outer sleeve, for example, by a cutting processing. Alternatively, the elastic hooks may also be mounted to the end of the outer sleeve by connecting mechanisms.

In order to limit relative rotation between the inner tube 6 and the outer sleeve 7, a circumferential limit mechanism is provided on the inner tube 6 and the outer sleeve 7. The circumferential limit mechanism includes a guide groove 6a formed in the side wall of the inner tube 6 extending in the axial direction, and a limit pin 7a located on the outer sleeve 7 and retained in the guide groove 6a. The side wall of the outer sleeve 7 is provided with a radial through hole 7b into which the limit pin 7a is fixedly inserted.

The guide groove 6a may extend through the side wall of the inner tube 6, or may be a blind hole which does not extend through the side wall of the inner tube 6. The axial length of the guide groove 6a may be determined based on the adjustment path of the guidewire.

In order to precisely adjust the axial position of the outer sleeve 7 relative to the inner tube 6, the inner tube 6 has an external thread in an axial middle portion thereof, where the driving sleeve 10 is engaged. The driving sleeve 10 has a threaded section 10a threadably engaged with the inner sleeve, and an extension section 10b mounted around the outer sleeve 7. The threaded section 10a and the extension section 10b are fixed to each other by a plug-in connection. An outer wall of the driving sleeve 10 has a textured surface to facilitate grip.

The extension section 10b is mounted around the outer sleeve 7 to increase the overall strength of the guidewire adjuster, thereby preventing the inner tube 6 and the outer sleeve 7 from being bent or even broken.

The threaded section 10a has an annular groove in an inner side at a joint with the extension section 10b, and the outer wall of the outer sleeve 7 has a positioning member 7c rotatably engaged in the annular groove. The positioning member 7c is an annular protrusion which is engaged in the annular groove. The limit pin 7a and the radial through hole 7b are provided at the annular portion, which has a greater thickness than the remaining portions, so that a loss of mechanical strength of the outer sleeve caused by the radial through hole 7b can be ignored.

When the driving sleeve 10 rotates relative to the inner tube, the driving sleeve 10 moves axially due to the threaded connection thereto, and drives the outer sleeve 7 and thus the guidewire to move axially relative to the control handle due to the engagement of the annular protrusion of the outer sleeve and the annular groove of the driving sleeve.

Figure 9:
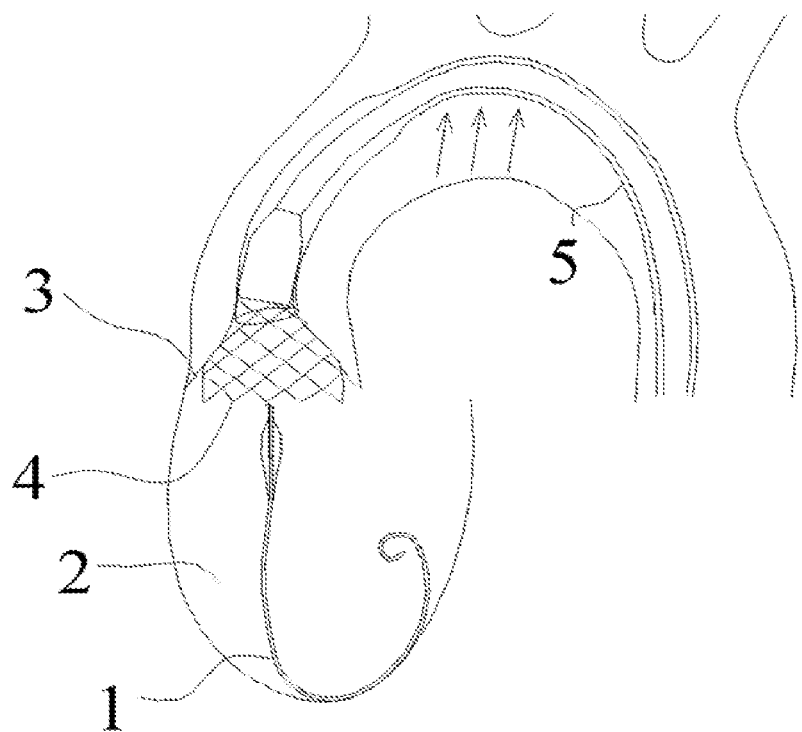
FIG. 9 is a schematic view showing the position of the stent having been adjusted by using the guidewire adjuster of the delivery system according to the present invention.

Referring to FIG. 9, taking the interventional aortic valve replacement procedure for example, a thin guidewire 1 is inserted into the body of a patient through the femoral artery or the femoral vein. The leading end of the guidewire 1 enters the left ventricle 2 through the aortic valve, and is partially coiled and rested at the bottom of the left ventricle. The sheath loaded with the valve is then delivered to the aortic valve 3 over the guidewire, and the sheath is withdrawn to release the stent 4. As the released stent 4 expands to a tapered expansion configuration, the tapered outer wall would slide down under the pressing of the aortic valve 3, which results in the valve on the stent 4 being positioned lower than expected.

The unsatisfactory deployed position of the valve on the stent 4 can be adjusted by the guidewire adjuster of this embodiment, the adjustment process of which will be described in detail hereinafter.

The guidewire adjuster and the control handle are first fixed through the connecting member in advance, then the driving sleeve is rotated, and the outer sleeve is driven to move via the engagement of the position member of the outer sleeve and the annular groove of the driving sleeve. As the limit pin on the outer sleeve is engaged in the guide groove of the inner tube, the outer sleeve is prevented from rotating relative to the inner tube, and thus the outer sleeve only slides axially when is driven by the driving sleeve.

The outer sleeve drives the guidewire to move relative to the control handle by the locking mechanism, in the meantime, the operator holds the operation handle and maintains the position of the operation handle as well as the position of the sheath. Therefore, as the guidewire is advanced by the guidewire adjuster, the portion of the guidewire entering in the blood vessel increases, and thus the length of the portion is increased. Since the leading end of the guidewire is supported at the bottom of the left ventricle, the elongated portion of the guidewire in the blood vessel would move in the direction as indicated by the arrow in FIG. 9 and drive the sheath to move outwardly at the bending portion of the aortic arch.

As the length of the sheath entering in the blood vessel does not increase, the distal end of the sheath (the end distant from the lesion site) is fixed relative to the operation handle, forcing the proximal end of the sheath to move outwardly with the guidewire at the bending portion. As a result, the movement of the sheath would drive the core shaft therein together with the stent to move upwardly along the direction as indicated by the arrows shown in FIG. 9 to adjust the position of the stent.

Figure 10:
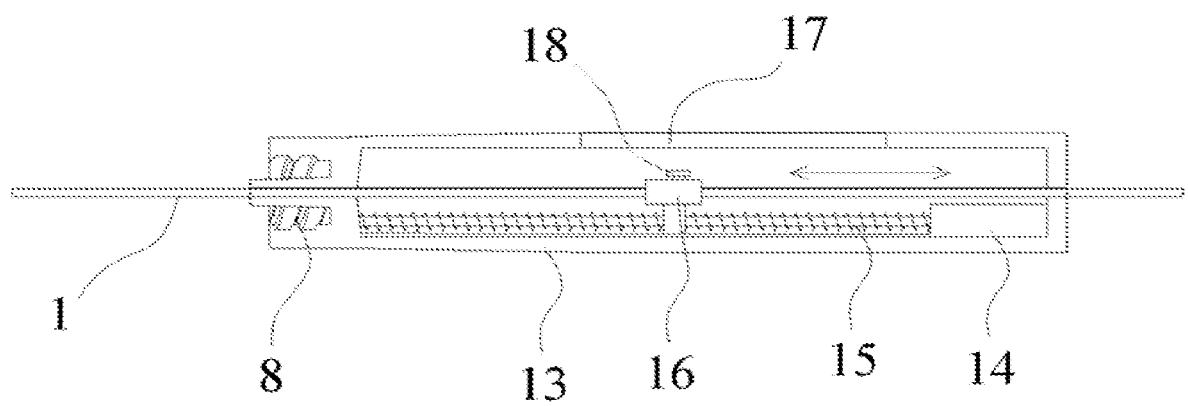
FIG. 10 is a schematic view showing an internal structure of an alternative guidewire driving mechanism according to the present invention.

Referring to FIG. 10, according to an another embodiment, a support mechanism is a tubular housing 13, one end of which is provided with a connecting member 8 connectable with the control handle.

The housing 13 has a lumen therein for the guidewire 1 to extend through, and the the guidewire extends linearly within the lumen. One end of the guidewire 1 passes through the housing 13 from the Luer taper portion and enters into the control handle, and the other end of the guidewire extends out from the housing 13.

A driving motor 14 acts as a driving mechanism of the guidewire, and is provided in the housing 13. A control button (not shown) of the driving motor 14 may be provided on the housing 13. An output shaft of the driving motor 14 is connected to a lead screw 15. The lead screw 15 is threadably engaged with a slide block 16 which is fixed to the guidewire 1.

Given the limited travel distance of the slide block 16, the slide block 16 is provided with a through hole in order to increase the range of movement of the guidewire, and the diameter of the hole is slightly larger than the diameter of the guidewire, that is, the guidewire is loosely fitted in the slide block 16. A locking screw 18 is provided which extends into an insertion hole of the slide block and abuts against the guidewire 1, and thus the guidewire can be locked or released by rotating the locking screw 18. For facilitating the operation of the locking screw 18, the housing 13 is provided with an opening 17 which may be closed by way of a flap shell or a sliding sleeve or the like.

During installation or advancement of the guidewire, the locking screw 18 can be first unscrewed and the guidewire 1 is able to move freely in the slide block. When precise adjustment is required, the guidewire 1 is locked by screwing in the locking screw, and then the movement of the guidewire 1 can be precisely controlled by the transmission mechanism. Specifically, the driving motor 14 drives the lead screw 15 to rotate, and the slide block 16 in turn drives the guidewire 1 to move linearly back and forth. A guide groove may be provided in the housing 13 for preventing the slide block 16 from rotating, and for guiding the movement of the slide block.

Figure 11:
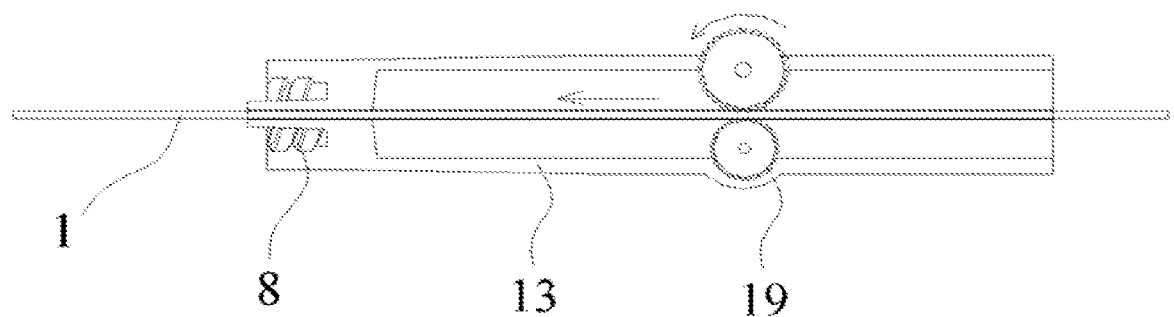
FIG. 11 is a schematic view showing an internal structure of another guidewire driving mechanism according to the present invention.

Referring to FIG. 11, according to a further embodiment, the support mechanism for the guidewire is a tubular housing 13, one end of which is provided with a connecting member 8 which is connectable with the control handle.

The housing 13 has a lumen therein for the guidewire 1 to extend through, and the guidewire extends linearly within the lumen. One end of the guidewire 1 passes through the housing 13 from the Luer taper portion and enters into the control handle, and the other end of the guidewire extends out from the housing 13.

Two wheels 19 are provided in the housing and act as the driving mechanism for the guidewire for cooperatively clamping the guidewire 1. One of the wheels is a driving wheel, and the other one is a driven wheel. In the case of manual driving, a portion of the outer edge of the driving wheel is located outside the housing 13 for a user to drive. In the case of electrical driving, a driving motor is provided in the housing 13, and the output shaft of the driving motor is engaged with the driving wheel by, for example, a gear transmission mechanism. In that case, both wheels can be entirely positioned in the housing, with only a control button of the driving motor provided on the surface of the housing.

What is claimed is:

1. A delivery system, comprising:
a guidewire;
a sheath having a lumen for accommodating a stent;
an operation handle connected to the sheath and the sheath is movable when driven by the operation handle, the operation handle having a first lumen for the guidewire to extend therethrough; and
a guidewire adjuster connected to a distal end of the operation handle, the guidewire adjuster has a portion connectable with the guidewire, the guidewire adjuster comprises:
a support mechanism configured as an inner tube, detachably connected to the operation handle, the support mechanism having a second lumen communicating with the first lumen of the operation handle; and a driving mechanism configured as an outer sleeve, movably connected to the support mechanism, and the driving mechanism is configured to be connected with the guidewire,
wherein one of the inner tube and the outer sleeve is provide with a connecting member at one end thereof, and another one of the inner tube and the outer sleeve is provided with a locking mechanism at an end distant from the connecting member, and the connecting member comprises a fitting structure fixedly connectable with the operation handle,
wherein the sheath is movable in a proximal direction by driving the operation handle to release the stent, and the portion of the guidewire adjuster is movable relative to the operation handle to drive the guidewire to move, so as to adjust a position of the sheath and thus the stent after the stent is released from the sheath.

2. The delivery system according to claim 1, wherein the support mechanism comprises a housing, through which the second lumen extends along a straight path or a curved path.

3. The delivery system according to claim 1, wherein at least a portion of the driving mechanism is located inside a housing of the support mechanism, or at least a portion of a housing of the driving mechanism is located outside the housing of the support mechanism.

4. The delivery system according to claim 1, wherein the driving mechanism comprises a force applying member in direct contact with the guidewire, and the force applying member is movable along the second lumen or rotatable about an axis, and the axis is arranged perpendicular to or inclined with respect to a corresponding portion of the second lumen.

5. The delivery system according to claim 1, wherein the connecting member has an internal thread engagable with a luer taper, or a plug that is connectable with the operation handle via a plug-in connection.

6. The delivery system according to claim 1, wherein one end of the inner tube is provided with the connecting member, and one end of the outer sleeve distant from the connecting member is provided with the locking mechanism.

7. The delivery system according to claim 6, wherein the locking mechanism comprises an axial bearing member detachably connected to the guidewire, and a driving member provided on the outer sleeve and connected to the axial bearing member, the axial bearing member is locked to the guidewire by a screw or fixed to the guidewire by elastic clamping.

8. The delivery system according to claim 6, wherein the locking mechanism is an abutting member inserted into a side wall of the outer sleeve, and one end of the abutting member extends into the second lumen to abut against the guidewire.

9. The delivery system according to claim 6, wherein the locking mechanism comprises at least two elastic claws at the end of the outer sleeve for clamping the guidewire, and a pressing cap threadably engaged with the end of the outer sleeve end to force the elastic claws to converge towards each other, an inner wall of the pressing cap comprises a tapered surface for guiding the elastic claws to converge towards each other, and the pressing cap is provided with a guidewire insertion hole at a central portion thereof.

10. The delivery system according to claim 1, wherein a circumferential limit mechanism is provided between the inner tube and the outer sleeve, the circumferential limit mechanism comprises a guide groove extending axially in a side wall of one of the inner tube and the outer sleeve, and a limit pin locating on another one of the inner tube and outer sleeve, and the limit pin extends into the guide groove.

11. The delivery system according to claim 1, wherein an outer thread of the inner tube is engaged with a driving sleeve, which is rotatably connected to the inner tube and axially positioned thereto, wherein the driving sleeve is provided with an annular groove at an inner wall thereof, and the outer sleeve is provided with a positioning member at an outer wall thereof, and wherein the positioning member is rotatably engaged in the annular groove.

12. A method for positioning a valve using the delivery system according to claim 1, the method comprising:
  inserting the guidewire into a body;
  advancing a leading end of the guidewire to a target chamber along a curved path until the leading end is rested at a bottom of the target chamber;
  delivering the sheath of the delivery system which is loaded with a stent into the body along the guidewire by means of the operation handle, until the stent reaches a target implant position;
  withdrawing the sheath to release the stent;
  driving the guidewire to move relative to the operation handle by operating the guidewire adjuster so as to adjust a position of the sheath and the stent.

13. The method for positioning a valve according to claim 12, further comprising locking the guidewire to the guidewire adjuster before driving the guidewire to move relative to the operational handle.

14. The method for positioning a valve according to claim 12, wherein the step of inserting the guidewire into a body comprises: inserting the guidewire into a ventricle of the body through a femoral artery or a femoral vein.

15. The method for positioning a valve according to claim 12, wherein the step of driving the guidewire to move relative to the operation handle comprises:
  maintaining a position of the sheath and driving the guidewire to move towards the target chamber relative to the sheath, thereby driving a proximal end of the sheath to move outwardly with the guidewire, so as to move the valve upward.

16. The method for positioning a valve according to claim 12, wherein the step of driving the guidewire to move relative to the operation handle comprises: moving the outer sleeve relative to the inner tube to drive the guidewire to move relative to the sheath.

* * * * *